(12) United States Patent
Zavrel

(10) Patent No.: US 11,278,763 B2
(45) Date of Patent: Mar. 22, 2022

(54) SYSTEM AND METHOD FOR TRAINING TONGUE AS A TREATMENT FOR OBSTRUCTIVE SLEEP APNEA

(71) Applicant: Cornell University, Ithaca, NY (US)

(72) Inventor: Erik Alexander Zavrel, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 172 days.

(21) Appl. No.: 15/392,630

(22) Filed: Dec. 28, 2016

(65) Prior Publication Data

US 2017/0182358 A1    Jun. 29, 2017

Related U.S. Application Data

(60) Provisional application No. 62/272,523, filed on Dec. 29, 2015.

(51) Int. Cl.
| | | |
|---|---|---|
| A63B 71/06 | (2006.01) | |
| A63B 23/03 | (2006.01) | |
| A61F 5/56 | (2006.01) | |
| A63B 21/005 | (2006.01) | |
| A63B 24/00 | (2006.01) | |

(52) U.S. Cl.
CPC ............ *A63B 23/032* (2013.01); *A61F 5/566* (2013.01); *A63B 21/005* (2013.01); *A63B 24/0087* (2013.01); *A63B 71/0622* (2013.01); *A63B 2071/063* (2013.01); *A63B 2071/0694* (2013.01); *A63B 2220/51* (2013.01)

(58) Field of Classification Search
CPC .......... A63B 23/032; A63B 2071/0694; A63B 2071/063; A63B 71/0622; A63B 24/0087; A63B 21/005; A63B 2220/51; A63B 21/0023; A61F 5/566; A61B 5/4818; A61B 2505/09; A61B 5/7264; A61B 5/486; A61B 2560/0209; A61B 5/743; A61B 5/228; A61B 5/682; A61B 5/4552; A61B 2560/0223
See application file for complete search history.

(56) References Cited

U.S. PATENT DOCUMENTS

| | | | | |
|---|---|---|---|---|
| 10,029,144 B2 * | 7/2018 | Noguchi | ............... | A63B 21/021 |
| 2003/0078521 A1 * | 4/2003 | Robbins | ................ | A61B 5/228 |
| | | | | 600/587 |
| 2003/0163065 A1 * | 8/2003 | Nakao | .................... | A61B 5/228 |
| | | | | 600/590 |
| 2007/0073168 A1 * | 3/2007 | Zhang | ................... | A61N 1/3627 |
| | | | | 600/483 |
| 2011/0057874 A1 * | 3/2011 | Al-Tawil | ............ | A63B 71/0622 |
| | | | | 345/156 |
| 2011/0130249 A1 * | 6/2011 | Mikhailenok | ........ | A63B 23/032 |
| | | | | 482/10 |

(Continued)

*Primary Examiner* — Sundhara M Ganesan
*Assistant Examiner* — Shila Jalalzadeh Abyaneh
(74) *Attorney, Agent, or Firm* — Foley & Lardner LLP

(57) ABSTRACT

The present disclosure describes systems and methods for the treatment of obstructive sleep apnea. The system includes a mouthpiece. The mouthpiece includes a force plate that a user can press against with their tongue. Pressing the force plate enables the user to strengthen their tongue. The system also includes a control module that can measure the force applied to the force plate and provide feedback to the user about progress and the applied force.

29 Claims, 5 Drawing Sheets

(56) References Cited

U.S. PATENT DOCUMENTS

| | | | | |
|---|---|---|---|---|
| 2012/0143091 A1* | 6/2012 | Annett | .................... | A61B 5/228 |
| | | | | 600/590 |
| 2013/0190656 A1* | 7/2013 | Toyota | .................. | G01L 19/149 |
| | | | | 600/590 |
| 2013/0296751 A1* | 11/2013 | Martin | .................... | A61H 21/00 |
| | | | | 601/148 |
| 2014/0342324 A1* | 11/2014 | Ghovanloo | .............. | G09B 5/06 |
| | | | | 434/185 |
| 2015/0045698 A1* | 2/2015 | Gribb | ........................ | A61B 5/08 |
| | | | | 600/587 |
| 2016/0144227 A1* | 5/2016 | Bell | ..................... | A63B 23/032 |
| | | | | 482/11 |

* cited by examiner

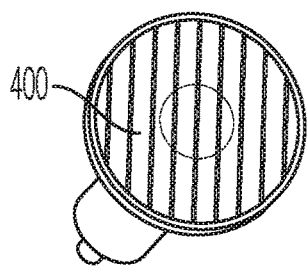 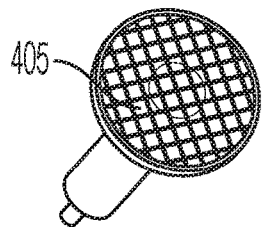 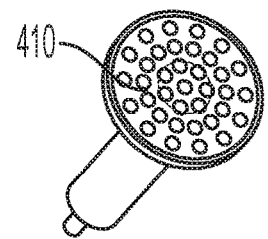
*FIG. 4A*     *FIG. 4B*     *FIG. 4C*
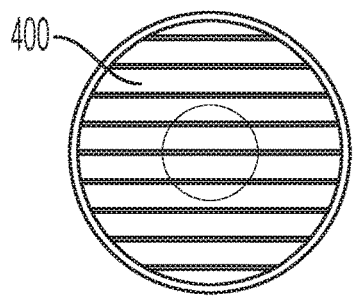 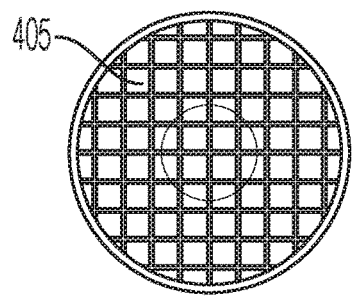 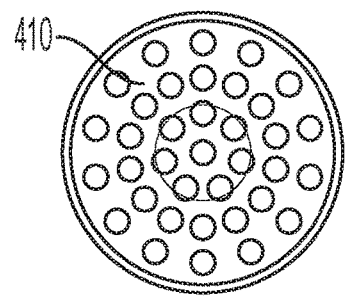
*FIG. 5A*     *FIG. 5B*     *FIG. 5C*

SYSTEM AND METHOD FOR TRAINING TONGUE AS A TREATMENT FOR OBSTRUCTIVE SLEEP APNEA

CROSS-REFERENCE TO RELATED APPLICATIONS

This application claims priority to U.S. Provisional Patent Application No. 62/272,523 filed on Dec. 29, 2015 and titled "SYSTEM AND METHOD FOR TRAINING TONGUE AS A TREATMENT FOR OBSTRUCTIVE SLEEP APNEA," which is herein incorporated by reference in its entirety.

FIELD

The present disclosure is directed to systems and methods for treatment of obstructive sleep apnea (OSA).

BACKGROUND

Obstructive sleep apnea (OSA) is a condition that can include temporary diminutions or cessations of breathing caused by repetitive collapse of the upper airway (UA) during sleep. OSA is a common disorder in which the muscles of the airway, which normally relax during sleep, fail to provide sufficient dilatory force to balance the contractive force from inspiratory activity. This force imbalance can collapse the UA either partially or completely, thereby preventing sufficient air from reaching the lungs. These pauses in breathing lead to blood oxygen desaturation and induce neurological arousal resulting in sleep disruption and fragmentation. The cycle of airway collapse and arousal can repeat hundreds of times per night.

OSA affects between 18 and 22 million Americans per year and is associated with physiological and psychological problems. OSA results in excessive daytime sleepiness, fatigue, memory impairment, and reduced reaction time, increasing the risk for motor vehicle and workplace accidents. In addition, OSA sufferers can face increased cardiovascular risk including hypertension, heart disease, and stroke. OSA has been recently linked to increased cancer incidence and mortality, presumably through hypoxia-induced angiogenesis. According to the National Sleep Foundation, 80% of the cases remain undiagnosed.

Existing treatments for OSA can include lifestyle modifications such as weight loss, position restriction, avoidance of muscle relaxants such as alcohol and benzodiazepine drugs, and oral appliances including mandibular advancement devices and tongue retaining devices. OSA is also treated through surgery. The most widespread and generally effective treatment for OSA, however, remains the use of various devices for maintaining positive airway pressure (PAP) such as Continuous Positive Airway Pressure (CPAP), BiLevel Positive Airway Pressure (BiPAP), and Autotitrating (AutoPAP) devices. CPAP and related treatments are costly and cumbersome. 40-60% of patients prescribed CPAP fail to adhere to the treatment. Patients cite comfort and lifestyle factors (sensation of claustrophobia, dry mouth, ill-fitting mask, and lack of portability of the system precluding use during travel) as reasons for abandoning treatment. Among older men, Benign Prostatic Hypertrophy (BPH), with accompanying nocturia, has also been associated with noncompliance with CPAP. Poor compliance with CPAP is prompting the search for alternative forms of treatment for OSA.

SUMMARY

Disclosed herein are systems and methods to train the Genioglossus (GG) muscle. GG muscle makes up most of the body of the tongue and is a major UA dilator, responsible for opposing the collapsing force in pharynx upon inspiration. Systems include, deploying a tongue-training device to strengthen the GG muscle, for the latter to dilate the pharyngeal pathway and thus prevent UA collapse.

According to one aspect of the disclosure, a device includes a mouthpiece. The mouthpiece includes a force transducer and a pusher plate. The pusher plate can be coupled with the force transducer. The pusher plate can be configured to transfer a force applied to the pusher plate to the force transducer. The device can also include a control module that includes at least one processor that is configured to receive a signal from the force transducer. The signal can indicate the force applied to the pusher plate.

The force transducer can be a piezoresistive compression load cell. The force transducer can have a dynamic range of between about 0 and about 25 lbf. A housing of the mouthpiece can include at least one of DELRIN, TEFLON, or polylactide plastic.

The mouthpiece can include one or more grooves configured to receive a user's tooth. The one or more groove can be angled between about 0 degrees and about 20 degrees. The pusher plate can be removable from the mouthpiece. The pusher plate can include a textured surface.

According to another aspect of the disclosure, a mouthpiece can include a force transducer and a pusher plate coupled with the force transducer. The pusher plate can be configured to transfer a force applied to the pusher plate to the force transducer.

The mouthpiece can include one or more grooves configured to receive a user's tooth. The pusher plate can include a textured surface. The mouthpiece can be disposable.

According to another aspect of the disclosure, a method can include providing a mouthpiece. The mouthpiece can include a force transducer and a pusher plate that is coupled with the force transducer. The method can also include providing a control module coupled with the mouthpiece. The method can include transferring, by the pusher plate, a force applied to the pusher plate to the force transducer. The method can include converting, by the force transducer, the force to a signal. The method can also include receiving, by the control module, the signal.

The force transducer can be a piezoresistive compression load cell. The force transducer can have a dynamic range of between about 0 and 25 lbf. A housing of the mouthpiece can include at least one of DELRIN, TEFLON, or polylactide plastic. The mouthpiece can include one or more grooves configured to receive a user's tooth. The one or more grooves can be angled between about 0 degrees and about 20 degrees. The pusher plate can be removable from the mouthpiece. The pusher plate can include a textured surface.

BRIEF DESCRIPTION OF THE DRAWINGS

FIGS. 4A-4C illustrate computer models of example textured surfaces of the pusher plate for use in the system illustrated in FIG. 1.

FIGS. 5A-5C illustrate manufactured examples of the computer models illustrated in FIGS. 4A-4C.

DETAILED DESCRIPTION

Herein described are systems and methods for training and strengthening the GG muscle, which serves to dilate the pharyngeal pathway. Restriction of the GG muscle can result in obstructive apnea during sleep. The present solution can be used by OSA patients who are unable to acclimate to CPAP or adhere to CPAP's use for comfort or lifestyle reasons.

The present solution can be used to provide regular exercise of the GG muscle to increase the tongue's maximum tongue protrusive force (TPFmax) and increases the time duration over which the tongue is capable of exerting sub-maximal (threshold of 50% of baseline TPFmax) protrusive force (dur50%). Regular exercise of the GG muscle can reduce the Respiratory Disturbance Index (RDI) during sleep. Regular exercise can also improve TPFmax, apnea hypopnea index (AHI), and RDI (the sum of apneas, hypopneas, and milder, more subtle sleep disruptions known as respiratory effort related arousals, or RERAs). Regular exercise can also improve dur50%, subjective sleep assessments such as the Epworth Sleepiness Scale and Fatigue Severity Scale, and snoring. An increase in TPFmax can be the result of increased strength of the tongue muscle. An increase in dur50% can be from decreased fatigability (increased resilience to fatigue) in the tongue muscle.

Figure 1:
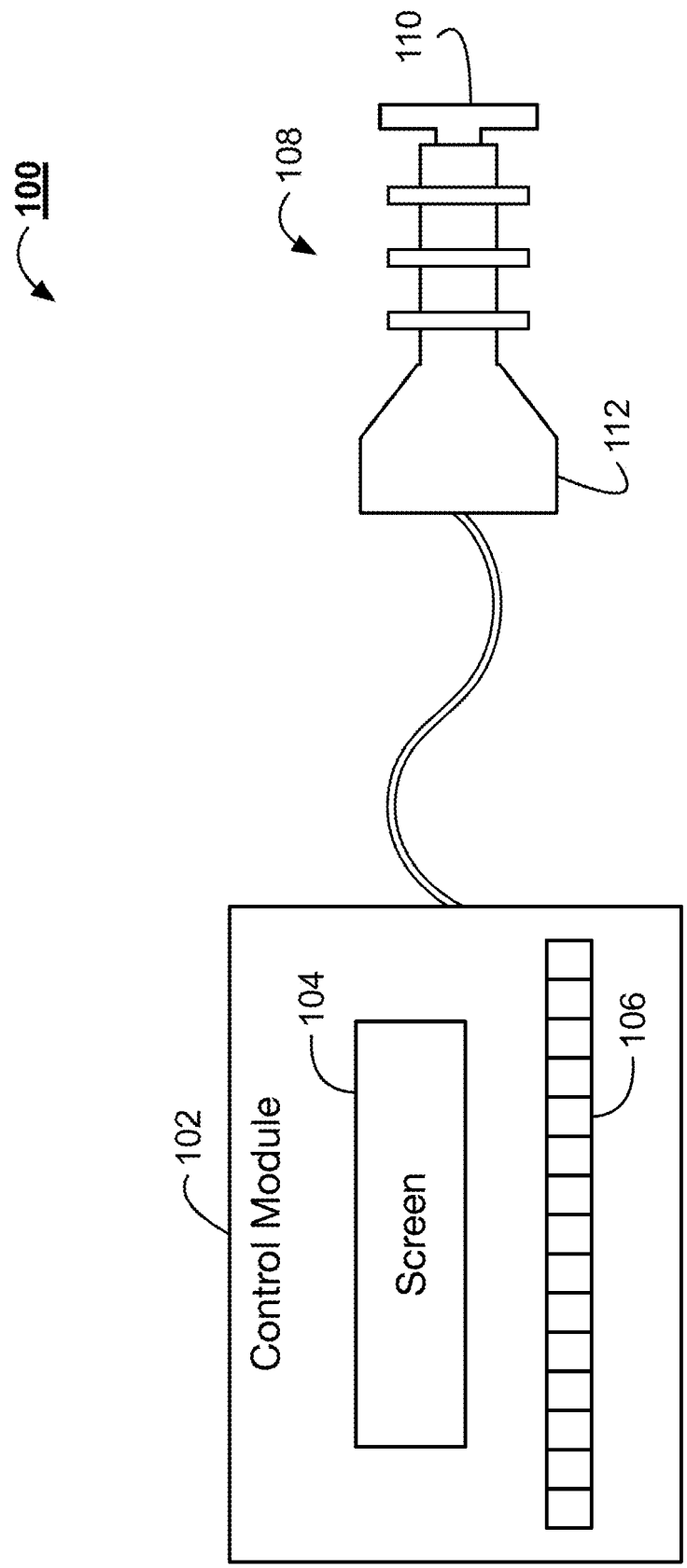
FIG. 1 illustrates a block diagram of an example system for strengthening the CG muscle.

FIG. 1 illustrates a block diagram of an example system 100 for strengthening the CG muscle. The system 100 includes a control module 102. The control module 102 includes a screen 104 and a secondary output array 106. The control module 102 is coupled to a mouthpiece 108.

The control module 102 can be a stand-alone device or an interface to a secondary computing device. The control module 102 receives electrical signals from the mouthpiece 108. The electrical signals can carry information from a transducer within a housing 112 of the mouthpiece 108. The information can indicate the amount of force applied to a pusher plate 110 of the mouthpiece 108. The amount of force applied to the pusher plate 110 can be displayed to the user via the screen 104 or the secondary output array 106. The secondary output array 106 can be a strip of colored, light emitting diodes (LEDs). The LEDs of the secondary output array 106 can be arranged from red, yellow, and then to green. As pressure is applied to the pusher plate 110, the LEDs can light up red when the force applied to the pusher plate 110 is not near the target force, yellow as the force nears the target force, and green when the force is within a target force range. In some implementations, the control module 102 can be a smart phone, tablet computer, laptop, or other mobile computing device. The control module 102 can be computer.

Figure 2:
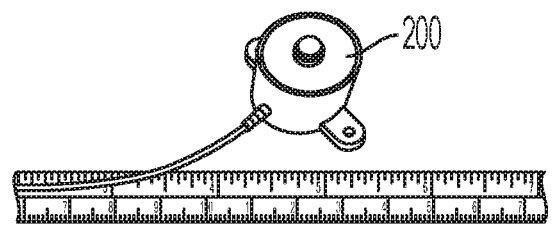
FIG. 2 illustrates an example transducer for use in the system illustrated in FIG.

FIG. 2 illustrates an example transducer 200. The transducer 200 can convert a force applied to a force plate into an electrical signal. The electrical signal can be an analog signal, the voltage of which is proportional to the applied force. In some implementations, transducer 200 can digitize the electrical signal and transmit a digital signal to the control module 102.

Figure 3:
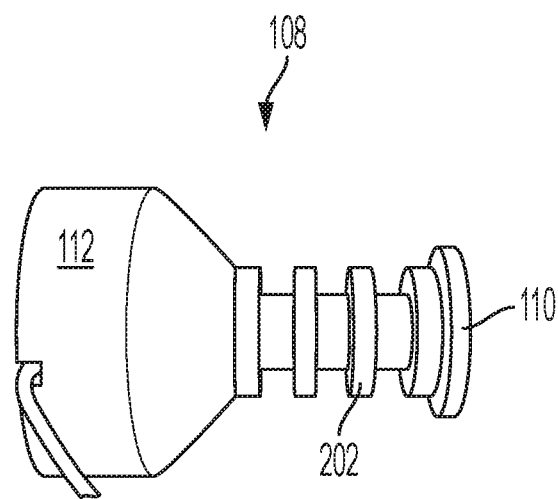
FIG. 3 illustrates an example mouthpiece for use in the system illustrated in FIG. 1.

FIG. 3 illustrates the mouthpiece 108. The force transducer 200 illustrated in FIG. 2 is contained within a lightweight housing 112. The housing 112 is configured to fit securely in a patient's mouth. The proximal end of the mouthpiece 108 is circumscribed by a set of three parallel grooves 202 into which the user places his incisor teeth, thus immobilizing the mouthpiece 108 during exertion and ensuring that the registered force is due to tongue action. The grooves 202 enable positioning of the pusher plate 110 (which serves as the target for tongue action) at different depths inside the oral cavity, allowing the user to exert differing amounts of force. Each groove can have a trapezoidal profile, with sidewalls angled between about 0 degrees and about 20 degrees, between about 5 degrees and about 15 degrees, or between about 5 degrees and about 10 degrees from the vertical. The angled sidewalls can facilitate guiding and placement of the teeth into a selected groove. The mouthpiece 108 is designed so that the tongue can act over a physiologically meaningful scale (nearly abutting the back of the incisor teeth). The pusher plate 110 can include a low friction plunger that can communicate the force applied to the pusher plate 110 to the load cell of the transducer. Due to the small diameter of the active button region of the transducer, a pusher plate can have a larger diameter as the target for tongue action. The diameter of the pusher plate's face can be between about 0.25 inches and about 1 inch, between about 0.5 inches and about 1 inch, and about 0.75 inches and 1 inch. In some implementations, the face of the pusher plate 110 is textured. In some implementations, the mouthpiece 108 is disposable, for example, the mouthpiece can be made from plastic and can be disposed of after one or more uses. In other implementations, the mouthpiece 108 includes metal and may be reused.

FIGS. 4A-4C illustrate computer models of textured surfaces of the pusher plate. FIGS. 5A-5C illustrate manufactured examples of the computer models illustrated in FIGS. 4A-4C. The pusher plate's face may be textured for greater traction to reduce slippage of the tongue off the plate (which may result in premature termination of a trial and not reflect true ability). FIGS. 4A and 5A illustrate a face 400 with a lined texture. FIGS. 4B and 5B illustrate a face 405 with a checkerboard pattern. FIGS. 4C and 5C illustrate a face 410 with circular dimples arranged in a circular pattern. The textured features can include bumps, studs, or other elevated patterns. The textured features can have a height of between about 0.01 inches and about 0.1 inches, between about 0.01 inches and about 0.06 inches, or between about 0.01 inches and about 0.04 inches.

In some implementations, the mouthpiece 108 is configured to weigh between about 20 grams and about 70. The mouthpiece can be machined by milling or injection molding. The mouthpiece can include DELRIN, TEFLON, or polylactide (PLA) plastic.

The force and pressure to hold the mouthpiece ensemble in place is much less than the maximum bite force capable of being exerted by a human jaw and much less than the force exerted during potentially dangerous episodes of clenching. The sensor can measure force applied to the load cell while the force necessary to hold the mouthpiece (containing the transducer in the base) is exerted by the teeth in a direction orthogonal to the force exerted by the tongue. The grooves 202 can enable user to avoid biting down hard, which can avoid jaw fatigue. The mouthpiece is configured to withstand the bite force (even extreme) of the user.

The transducer outputs an analog signal (0-5 V) proportional to the applied force. An analog-to-digital converter (ADC) in the control module (or mouthpiece) digitizes the signal for processing.

The number of discretized/quantized levels provided by an ADC is related to the ADC's resolution: Number of quantized levels=2n, where n is the bit resolution of the ADC.

Therefore, an ADC can approximate the input analog voltage it samples as one of 2n levels. Each measured voltage gets rounded to one of 2n discrete values.

The step size is the amount of the voltage range covered between each of these discrete values. As step boundaries are defined by the 2n levels, there are 2n−1 steps.

The step size is the minimum change in input, which can be resolved by the ADC and is given by: Input Range/(2n−1)

For the standalone system, a 12-bit ADC (LTC1298) can be used. With a 25 lbf load transducer, the step size is:

$$25 \text{ lbf}/2^{12}-1 \quad 25 \text{ lbf}/4096-1 \quad 25 \text{ lbf}/4095$$
$$0.0061050061 \text{ lbf}=2.76918 \text{ gf}$$

The 12-bit ADC can resolve differences in applied force as small as 2.77 gf. Thus, the 12-bit ADC can discriminate between two applied forces that are closer in magnitude than 3 gf, making possible discerning even very small increases in force strength.

For a 10-bit ADC, with a 25 lbf load transducer, the step size is:

$$25 \text{ lbf}/2^{10}-1 \quad 25 \text{ lbf}/1024-1 \quad 25 \text{ lbf}/1023$$
$$0.02443792766 \text{ lbf}=11.0849 \text{ gf}$$

The 10-bit ADC can resolve differences in applied force as small as 11.1 gf. It can be seen the resolution difference factor between two ADCs, with resolution of n1 and n2 (where n2>=n1) is approximately related through 2n2−n1

In the above examples, the 12-bit system has $2^{12-10}=2^2=4$ times the resolution as the 10-bit resolution.

Figure 6:
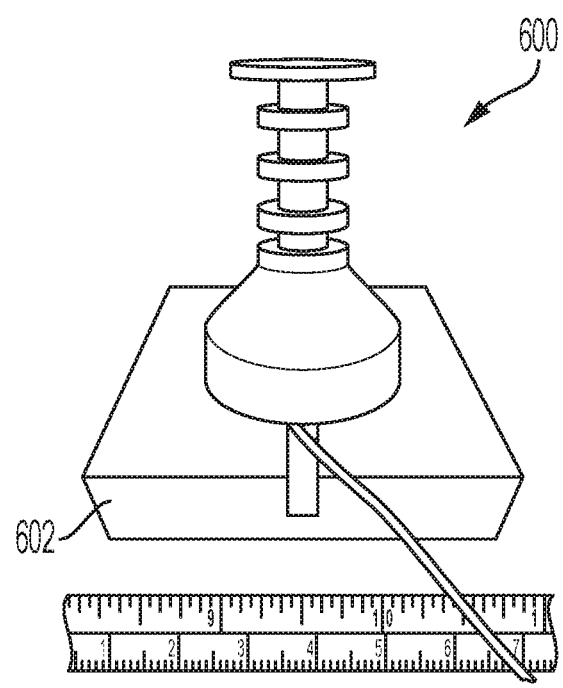
FIG. 6 illustrate an example system for calibrating the system illustrated in FIG.

The transducer can be calibrated. FIG. 6 illustrate an example system 600 for calibrating the transducer. Calibration of the transducer can provide a more accurate conversion of the raw ADC data to actual force data. Calibration can be performed using a set of standardized weights that were prepared using a laboratory balance. During the calibration procedure, the transducer and mouthpiece ensemble is placed in a dock 602 to hold the mouthpiece in a stationary and upright position. The weights are placed on the center of the pusher plate and the data logged automatically. A linear relationship was obtained and the values obtained from linear regression were inserted into the program(s) for automatic conversion of raw ADC data to processed force values.

Figure 7:
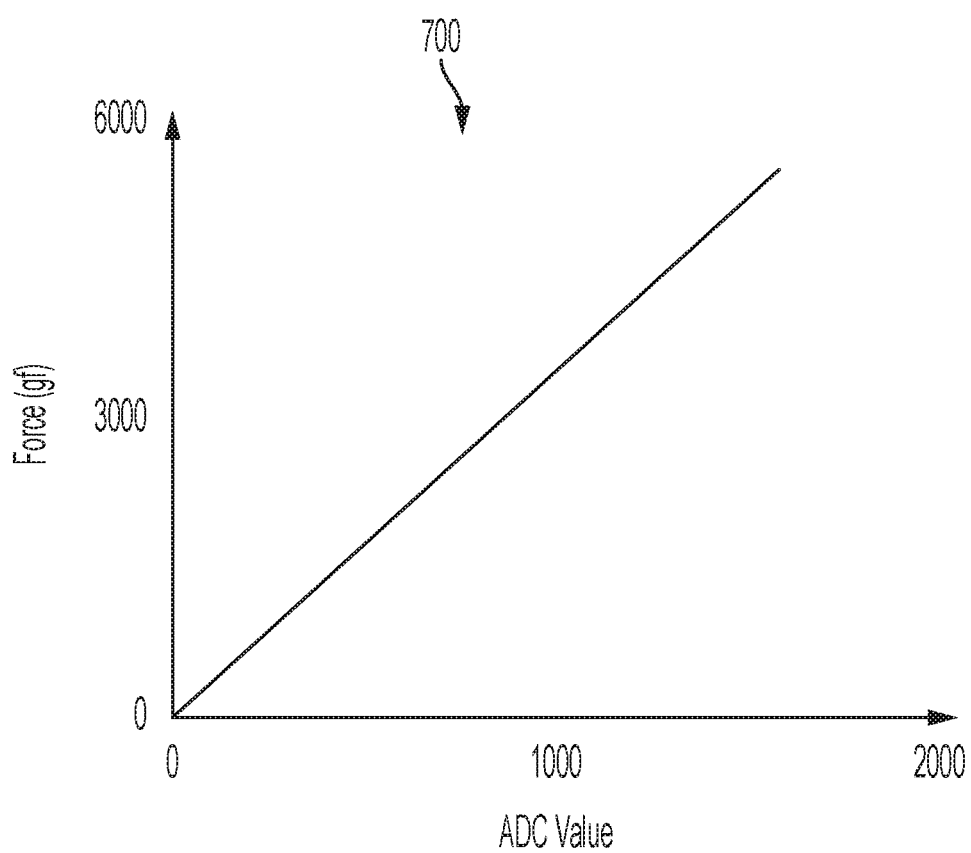
FIG. 7 illustrates a plot of a calibrated transducer signal compared to force.

FIG. 7 illustrates a plot 700 of a calibrated ADC data to force. In some implementations, the transducer can have a non-zero offset, meaning that its output with no force applied is non-zero (about 0.3 V). This offset is nearly identical from sensor to sensor but drifts slightly with environmental conditions like ambient temperature. Were offsets not accounted for, the system could provide an incorrect measurement of the applied force. The offset can be accounted for by subtracting slightly more than the largest recorded offset from the raw ADC value before measuring applied forces. A slightly larger than the largest recorded offset is subtracted in the event that the offset drift increases. A force sensor offset determination routine can be performed each time the system is used. For example, the control module can measure the offset 100 times over the period of a calibration phase, and can use the largest obtained offset as the value to be subtracted from the raw ADC output. If the subtracted offset exceeds the ADC value, then rollover can occur (for select variable types, this means the value can appear as a large positive number rather than a small negative number). A check can be performed to ensure this does not happen.

To quantitatively track changes in GG strength and fatigability over time, the control module can stamp the collected data with the date and time of acquisition. Moreover, the Tongue Trainer forces a TPFmax and dur50% run each week (every 7 days). Stamping files with the date and time and keeping track of the number of days that have elapsed since a TPFmax run was last conducted can use a real-time clock (RTC). The control module 102 can include a discrete time-keeping chip (e.g., the DS1302). In order to keep time, the control module can include a 32.768 kHz pacing crystal. It can use an auxiliary 3 V CR2032 lithium coin cell to power it when disconnected from the main power supply.

The collected data can be saved for later analysis by the control module. The data can be stored on the control module (e.g., in a removable memory card) or transmitted to a secondary computing device (e.g., a laptop computer). In some implementations, the data can be streamed to a remote storage facility where the data can be reviewed at a later date. In some implementations, a physician or caretaker can access the data. In some implementations, the data is written to EEPROM of the control module. The data can then be dumped to an external drive at the conclusion of the run. The control module can include an embedded USB host controller configured for UART mode to allow the control module to communicate with a USB mass storage device such as a flash drive via Simple Serial Interface (SSI). The control module can use the 8.3 file naming format convention. This means that file names can include 8 characters and a 3 letter file extension (.txt). Because of the limitations imposed by this file name length, in order to unambiguously stamp files with the greatest degree of temporal resolution, the adopted naming convention for files corresponding to training runs, e.g., runs other than TPFmax and dur50% runs, was: "MMDDHHmm.csv"

Where MM is the 2 digit month, DD is the 2 digit day, HH is the 2 digit hour in military mode, and mm is the 2 digit minute.

The flash drive can be coupled with the control module before turning on the control module. If no drive is detected, the control module can display a on the screen.

In some implementations, the control module can be configured to prompt the user to perform a plurality of exercise programs or trials. The control module can prompt the user to complete the exercise a predetermined number of time. For example, the control module, via the screen, can prompt the user to repeat an exercise 10 times (or to perform 10 repetitions of the exercise). After the conclusion of all exercises, the screen can indicate to the user that it is safe to turn off the system.

The control module can provide feedback to the user. For example, using the screen or the secondary output array (or by some sensory indication such as a speaker), the system can indicate to the user if the user is succeeding in exerting more force. The applied force can be conveyed to the user in a variety of different ways, including a high-resolution tricolor LED display, an LCD screen, a real-time plotting program, and a piezoelectric buzzer. For example, the applied force can be displayed visually to the user through the secondary output array, which can include a multiplexed system of 60 LEDs. The secondary output array can include six 10-segment LED bar graph displays arranged in an intuitive color-coded manner (2 red for the low end, 2 yellow for the middle range, and 2 green for the high end). A MAX7219 multiplexer (MUX) can be used to control the 60 LEDs. If a single bar graph display had been used, the user might not see any additional LEDs activate despite substantially increasing tongue strength and end up discouraged, potentially decreasing compliance with the training. For instance, with a 25 lbf load cell and the display represent the entire possible force range (0-25 lbf), each segment of a 10 segment display would represent 2.5 lbf while each segment of a 60 segment display would represent only 0.42 lbf. Display resolution is increased by the display represent less than the entire possible force range. The display is configured for an upper limit of 9999 gf (about 22 lbf). If a force greater than 9999 gf is applied to the load cell, the display saturates. For training runs, the lower limit of the display can be set to the threshold (percentage of baseline TPFmax) that can be exceeded in order for a run to commence, rather than zero.

In some implementations, the resolution can be increased by limiting the range over which the system measures force. For example, the maximum force can be set to the user's TPFmax. In this example, the upper limit of the display can be set to the baseline TPFmax or the weekly TPFmax, whichever is larger. In this way, the upper limit of the display increases along with gains in TPFmax. In some implementations, the threshold is a percentage of the baseline TPFmax (and not weekly TPFmax) such that the force that corresponds to a particular threshold (percentage) is constant throughout the duration of training. As the range to be displayed (the difference between the lower and upper limit, e.g., the difference between threshold and TPFmax) decreases, the resolution of the display increases. This means the display can seem more responsive at higher difficulty levels, responding strongly to even small changes in applied force. Thus, at higher difficulty levels, e.g., 50%, it may seem harder to maintain a certain force with the number of segments illuminated changing substantially with even small changes in applied force. In some implementations, the screen is refreshed at a faster rate (>30 Hz) than at which data is logged (10 Hz) to make it appear responsive and not sluggish to changes in applied force.

The screen can display user prompts and provides real-time feedback by displaying the current force and elapsed time of each run (with a resolution of 100 ms) so the person knows how long a run has lasted while he is exerting. Digital displays can be used when the value of interest is stable. To discern direction of change in a value, alternatives—such as the secondary output array can be used. The secondary output array can change from red to green to signal the subject to begin exertion and changes from green to red to signal the subject to end exertion either when run time (3 s for TPFmax runs and 4 min 30 s for training runs) is up or when the subject falls below threshold during a training run. Data can also be plotted in real time for viewing by the user. Data can be automatically plotted as it arrives. In some implementations, a piezoelectric buzzer provides aural cues to signal the subject to end exertion either when run time (3 s for TPFmax runs and 4 min 30 s for training runs) is up or when the subject falls below threshold during a training run.

In some implementations, the control module can include one or more pushbuttons to enable user input, allowing the subject to make menu selections, including choosing the device mode, entering the groove number, selecting the training threshold, confirming/setting the baseline TPFmax, and confirming dur50% runs. The control module can include one or more processors. One of the processor's auxiliary input/output (I/O) pins can be configured to read the state of the pushbutton. The processor can switch from main I/O to auxiliary I/O to poll the pushbutton and then switch back to main I/O. When not pressed, a 10 kilo-ohm pull-down resistor provides the I/O pin a reference to ground (low state or 0) and when pressed, the I/O pin senses a connection to power (high state or 1) through a 220 ohm resistor. Switch debouncing and distinguishing between menu scrolling and selection (a function of how long the button is pressed) are handled in the code executed by the processor.

The processor can generate a startup menu for display on the LCD screen after turning on the system and the user is asked to select the device mode. One mode can include "normal mode." Another mode, "test mode" can enable the user to force a TPFmax and dur50% run on demand, rather than waiting for 7 days to elapse. Test mode may be used during visits to a sleep lab or other care provider. In some implementations, to confirm a selection, the pushbutton is pressed for an extended period of time—for example 1 s. The cursor on the screen can flash for 2 s to indicate the selection has been confirmed. "Clear Memory" is selected to clear device memory of an established baseline in order to prepare the device for a new user or to establish a new baseline. After choosing to clear the device memory, the program can ask for confirmation in the event that the user accidentally chose that option or changed his mind. Choosing "Y" can clear the memory, reset the device, and welcome the subject as a new user. Choosing "N" can return the user to the startup menu. Every time the pushbutton is pressed and released, the choice can toggle from "N" to "Y" and back to "N." To confirm a selection, the pushbutton needs to be pressed for 2 s. The cursor on the screen can flash for 2 s to indicate the selection has been confirmed.

The pushbutton or other input device can be used for entering the groove number at which a run can be conducted. Every time the pushbutton is pressed and released, the groove setting can change. It can cycle from 1 to 3 (or the total number of grooves on the mouthpiece) and back to 1. Groove 1 corresponds to the groove closest to the plate against which the tongue is applied. Groove 3 corresponds to the groove farthest from the plate (also corresponds to having the device as deep inside the mouth as possible). To confirm a selection, the pushbutton is pressed for an extended period of time (e.g., 1 second). The cursor on the screen can flash for 2 s to indicate the selection has been confirmed. The pushbutton can also be used for selecting the threshold for training runs. For example, when the pushbutton is pressed and released, the threshold (percentage of baseline TPFmax) cam change. The threshold can cycle from 5% to 50% and back to 5%. To confirm a selection, the pushbutton is pressed for 1 s. The cursor on the screen can flash for 2 s to indicate the selection has been confirmed. After the first TPFmax run, setting of the baseline can be confirmed using the pushbutton. If the user is unsatisfied, "N" is selected to attempt the TPFmax run again. If satisfied, selecting "Y" can set the baseline TPFmax. Every time the pushbutton is pressed and released, the choice can toggle from "N" to "Y" and back to "N." To confirm a selection, the pushbutton is pressed for 1 s. The cursor on the screen can flash for 2 s to indicate the selection has been confirmed.

After a dur50% run, the user can be asked to save the data or attempt the trial again. This is for several reasons. First, dur50% runs can include a single trial unlike TPFmax runs, which can include three attempts, each of 3 s duration and separated by 30 s, with the TPFmax the greatest of the three exertions. Second, an exertion of 50% of baseline TPFmax can be difficult for some user to maintain. For this reason, premature failures—caused by a user momentarily dropping below threshold immediately after exceeding it—can occur. It would be undesirable to have these false starts reported as valid data. If the user is unsatisfied, "N" is selected to attempt the dur50% run again. If satisfied, selecting "Y" can save data from that dur50% run. This process can be repeated until the user is satisfied that the duration reflects true ability.

The control module can be implemented on a four-layer printed circuit board (PCB). A four-layer PCB can include internal power and ground planes for the routing of power and ground connections. The group and power planes can enable a compact layout, improved noise reduction, and ADC signal accuracy improvement. In the final PCB layout, Manhattan (right-angle wiring) was employed. Manhattan wiring features vertical traces on one layer and horizontal traces on another with vias (plated through-holes) added where necessary to connect a horizontal trace to a vertical trace. The input interconnects are aligned to a grid and the circuit connects to them perpendicularly.

Trace width on the PCB was reduced to allow for a compact layout but not be so narrow as to possess too high a resistance for current-carrying applications. Traces that carry significant current can be wider than signal traces. For example, the bar graph display traces can be 0.015". The inter-trace spacing can be between 0.007" and 0.01" (or more). For 0.015" wide traces and 0.031" wide vias, the inter-trace spacing can be set to 0.050" as 0.025" is inadequate:

Clearance between trace edges=inter-trace spacing−2 (trace width/2)=inter-trace spacing−trace width=0.025"−0.015"=0.010"

Clearance between trace edge and via=inter-trace spacing−via diameter/2−trace width/2=0.025"−0.031"/2−0.015"/2=0.025"−0.0155"−0.0075"=0.002"

Which is less than the suggested clearance of 0.010" and less than the minimum clearance of 0.007" An inter-trace spacing of 0.025" would not suffice even if 0.010" wide traces were used:

Clearance between trace edges=inter-trace spacing−2 (trace width/2)=inter-trace spacing−trace width=0.025"−0.010"=0.015"

Clearance between trace edge and via=inter-trace spacing−via diameter/2−trace width/2=0.025"−0.031"/2−0.010"/2==0.025"−0.0155"−0.005"=0.0045"

Which is less than the suggested clearance of 0.010" and less than the minimum clearance of 0.007"

Therefore, 0.050" inter-trace spacing can be used:

Clearance between trace edges=inter-trace spacing−2 (trace width/2)=inter-trace spacing−trace width=0.050"−0.015"=0.035"

Clearance between trace edge and via=inter-trace spacing−via diameter/2−trace width/2=0.050"−0.031"/2−0.015"/2=0.050"−0.0155"−0.0075"=0.027"

Which is greater than to the minimum clearance of 0.007" and greater than the suggested clearance of 0.010".

When narrow (0.010" and 0.015") traces were placed, abrupt right angle bends were avoided to prevent undercutting during the board manufacturing process. Instead, these traces were redirected using two 45 degree bends with a short straight trace in between.

The control module can monitor power consumption of the system. The system can include a battery, and the control module can monitor the battery level during operation of the system. The battery level can be monitored upon startup and immediately prior to the saving of data. When the battery level gets low, the control module can display a warning message on the screen. In some implementations, the system can use 6 AA batteries or a rechargeable battery pack. For voltage monitoring and regulating purposes, a battery that can maintain its nominal output voltage until nearly fully discharged can be used and can result in less frequent battery replacement. In some implementations, the current consumption of the system can be between about 225 mA to about 325 mA. Using the system for 30 minutes a day means the batteries should last about 3 weeks before needing to be replaced. To conserve power, the system can automatically turn off when not in use.

The main power switch of the system can be protected with a simple flip cover, which keeps the control module from being accidentally turning on while being transported in a purse or bag, which would drain the batteries and possibly log spurious data. The voltage from the battery pack (9 V nominal) can be regulated with a 7805 voltage regulator to 5 V for power distribution. For proper operation, the source voltage from the battery pack can be higher than the regulated output voltage by about 1.5 V. The ADC (LTC1298) used to digitize the force sensor signal has two channels and can monitor two inputs. However, the second channel can't be used to monitor the source voltage level as the ADC can't monitor a voltage greater than which it is being powered (5 V). Thus, a dedicated brownout detector can be used. As the 7805 voltage regulator can use a source (input) voltage about 1.5 V higher than its output (5 V), the brownout detector can be used to trip at about 6.5 V. Setting the threshold higher than necessary, e.g. 7 V, can result in having to change the batteries too frequently. However, commercially available brownout detectors (TC54) are designed with a threshold level of 4.3 V (their output logic state toggles at 4.3 V). The solution was to use a voltage divider with resistor values such that when the source voltage is 6.5 V, the brownout detector input sees 4.3 V:

$V\text{in}=V\text{source}*R1/(R1+R2)$

To maintain accuracy, the bleeder current through the divider should be significantly higher than the 1 μA operating current used by the TC54 chip. The minimum recommended bleeder current through the voltage divider is 100 μA (100 times the 1 μA used by the TC54). The resistor values for the voltage divider were calculated for 10 times this minimum suggested value, e.g., 1000 μA:

$i\text{bleeder}=V\text{source}/(R1+R2)$ $R1+R2=V\text{source}/i\text{bleeder}$ $R1+R2=6.5\text{V}/1000\ \mu\text{A}$ $R1+R2=6.5\text{V}/1\ \text{mA}$ $R1+R2=6.5\text{V}/10\text{-}3\ \text{A}$ $R1+R2=6500\ \text{ohm}$ $V\text{in}=V\text{source}*R1/(R1+R2)$ $V\text{in}/V\text{source}=R1/(R1+R2)$ $R1=V\text{in}/V\text{source}*(R1+R2)$ R1=4.3 V/6.5 V*6500 ohm R1=4300 ohm R2=6500 ohm−4300 ohm=2200 ohm A 2.2 kilo-ohm fixed resistor was used along with a 10 kilo-ohm multi-turn precision potentiometer. The potentiometer was adjusted until the brownout detector output changed when the source voltage was 6.5 V. One of the control module's processor's auxiliary input/output (I/O) pins is connected to the output of the brownout detector. The processor can switch from main I/O to auxiliary I/O to poll the brownout detector and then switch back to main I/O. Loading of the voltage regulator can result in a momentary drop in the voltage supplied to the board (e.g., a brownout). This loading effect occurs primarily due to the bar graph display, owing to which the current consumption can increase by 100 mA, from 225 mA to 325 mA (about 50%) over a very short period of time (a few tens of ms).

To eliminate fluctuations in the voltage supply, the circuitry of the control module can include a large (e.g., 1000 g) capacitor between the voltage regulator output and ground. The addition of this capacitor keeps the voltage from the regulator stable and prevents brownouts.

In some implementations, the system can be powered via a USB Male A to Male B cable or wall power supply.

The control module can be web-enabled. The control module can communicate with a remote server via a network to stream data so clinicians can view the data in real-time, remotely monitor treatment compliance, and make refinements to the training regimen. The clinician can remotely make adjustments to the patient's training regimen (such as the training difficulty level) simply by updating a settings file that is loaded by the control module at the time of execution. The data may be encrypted prior to uploading to the cloud.

Figure 8A:
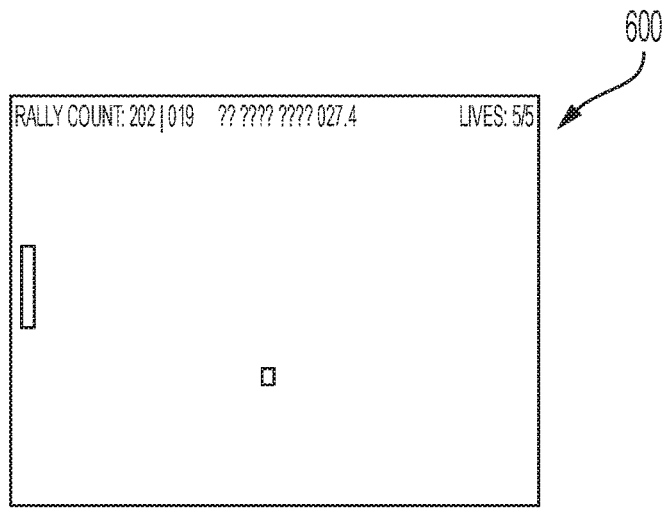
FIGS. 8A-8D illustrate examples of applications with which the system illustrated in FIG. 1 can interact.
Figure 8B:
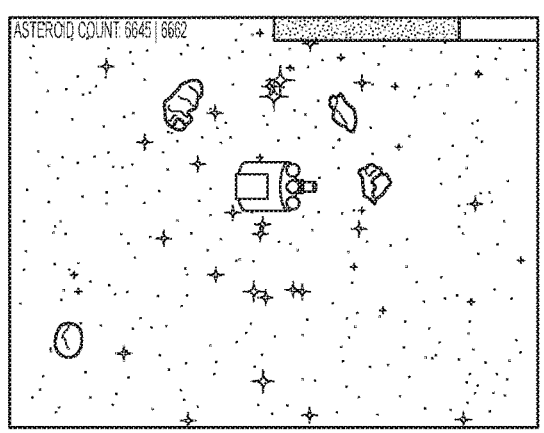
Figure 8C:
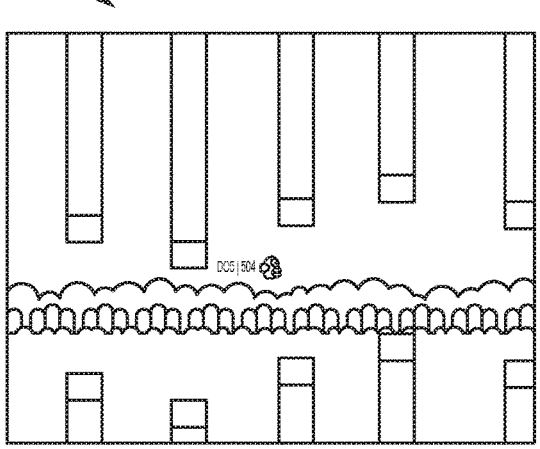
Figure 8D:
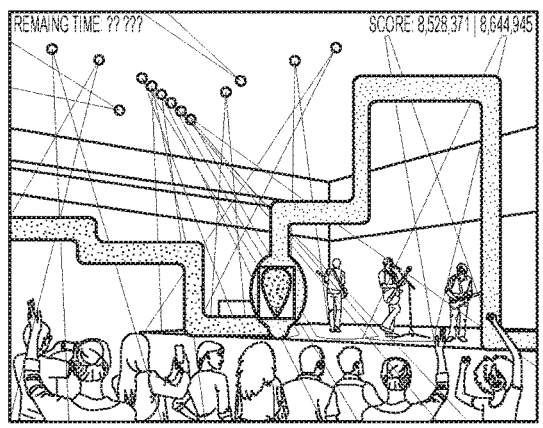

In some implementations, the system can be used as an input to a computer program or other application. FIGS. 8A-8D illustrate examples of applications the system can interface with. Using the system as an interface to an application can user engagement with the system. FIG. 8A illustrates the application pong being controlled with the system. FIG. 8B illustrates the application Asteroids being controlled with the system. FIG. 8C illustrate the application Flappy Bird being controlled with the system. FIG. 8D illustrates the application Guitar Hero being controlled by the system. The game difficulty can be automatically indexed against the player's ability, meaning gameplay is uniquely tailored to the individual. All game controls can be indexed against a user's baseline TPFmax. Interactive games are more able to engage patients and quantifying progress as a game score is an effective way to motivate and incentivize patients by appealing to their competitive spirit. For each of the applications, the control module can convert the force applied to the mouthpiece into a movement of an object in the application.

Because training can occur at different thresholds and different mouthpiece configurations, the control module can provide desired subsets of the data for valid comparison between runs. This can enable users and doctors to track progress and clinicians and researchers to quickly compare data gathered under the same conditions, e.g., durations of runs with a threshold of 5% at groove 2 or durations of runs with a threshold of 10% at groove 1.

EXAMPLES

An example study with the system described herein can include approximately 30 patients with previously documented moderate to severe OSA. They can receive an all-night in-laboratory sleep study to document the severity of their OSA immediately before starting the training regimen. Scales and questionnaires measuring sleepiness, snoring, fatigue, and insomnia can be administered prior to starting the training and repeated after six weeks of training. The principal measure of the efficacy of the treatment can be the change in RDI, the number of abnormal breathing events per hour of sleep. Working the tongue to the point of fatigue and achieving a substantial feeling of muscle burn is the goal of each effort trial. The burn is felt inside the throat, from under the chin to the Adam's apple where most of the GG is located. A burning sensation in the base of the tongue is indicative of strong muscle recruitment and is desirable for the purposes of this study.

A typical training regimen can include performing 10 successful trials, twice daily (once in the morning and once in the evening), seven days per week, for 6 weeks. The total training commitment time can be about 20-30 minutes per day. It is expected that subjects can have an acclimation period of several days before they become comfortable and competent with the training. The training regimen is personalized by indexing difficulty against a user's baseline maximum tongue protrusive force (TPFmax), the maximum force the user is capable of exerting at the onset of the training regimen. During the six weeks of training, subjects are able to set the minimum threshold force to be maintained from 5% to 50% of baseline TPFmax. Initial training (including selection of a comfortable setting) can occur under the guidance and supervision of a researcher in the sleep lab. Tongue fatigability can be used to guide the training threshold. Low to no fatigability at a certain threshold can suggest an increase in the training threshold. Quick fatigability at a certain threshold can suggest a decrease in the training threshold. We anticipate users can begin training at a threshold of 5% of baseline TPFmax and may progressively increase to 10 or 15% over time. Threshold setting can be a passive measure. The device does not act upon the user with a certain intensity nor force users to maintain exertion at a certain level. A run does not commence until the subject exceeds the selected threshold: if the setting is too high, the subject can simply be unable to exceed threshold and unable to initiate a trial.

The study can use a system similar to the systems described herein. The system can include a force transducer in the form of a Measurement Specialties FC22 piezoresistive compression load cell with a dynamic range of 0-25 lbf. Force is displayed and recorded in units of gram-force (gf). A gram-force is the force exerted on a mass of 1 gram under an acceleration of 1 g. 1 gf=9.807 milli-Newtons (mN).

The Measurement Specialties FC22 piezoresistive compression load cell (and mouthpiece) connected to the control module via a 2' cable. The cable can include three separate wires: power, ground, and signal. The cable terminates in a standard 4-pin male Molex connector, which in turn mates with a complementary 4-pin female Molex connector embedded within the control module. The Molex connectors are polarized to ensure proper orientation and prevent accidental connection reversals. Cylindrical conductive male pins in the male Molex connector mate with cylindrical conductive female sockets in the female Molex connector. The pins and sockets are held in a rectangular matrix in a nylon shell. The pins and sockets are glued in place to keep them from shifting and misaligning from repeated use (connecting and disconnecting). The sensor cable connector is protected and rendered durable by building up several successive layers of spray-on rubber.

As outlined above, existing treatments for OSA include lifestyle modifications, oral appliances, UA surgeries, hypoglossal nerve stimulators, and most frequently, CPAP and related devices. Oral appliances as well as surgical approaches target specific obstructing airway structures and are best used in patients who present with circumscribed anomalies, such as a degree of retrognathia in the case of a mandibular advancement device or redundant oropharyngeal tissue in the case of UPPP. Success rates for these interventions are therefore dependent upon careful pre-screening.

The typical risks of surgery are magnified in OSA patients due to a variety of factors. This patient population as a whole has higher rates of obesity, with all the risks this condition presents. Furthermore, OSA patients are predisposed to oxygen desaturation and are particularly sensitive to anesthesia. Recent reports show these patients suffer increased apneic episodes while under anesthesia. As a result of the paralyzing effect of anesthesia on airway muscles, patients with OSA are at high risk of developing complications when having surgery or other invasive interventions under general anesthesia, whether or not the procedure is related to OSA The standard treatment for OSA is CPAP, which involves wearing a mask and hose that deliver a stream of pressurized air, acting as a splint to keep the airway open. Except in rare cases such as patients with pneumothorax, the use of CPAP presents minimal direct risks. However, 40-60% of those prescribed CPAP, stop using it, citing factors like discomfort, claustrophobia, dry mouth, and difficulties traveling with the apparatus. Furthermore, the definition of what constitutes compliance with CPAP is fairly liberal, perhaps in acknowledgement of the challenges of treatment. For example, to qualify for Medicare reimbursement, new patients can average only four hours of use nightly during their adaptation period.

Those with Down syndrome (DS) are prone to developing OSA for a variety of reasons, including an abnormally small UA, micrognathia, enlarged adenoids and tonsils, and low muscle tone in the mouth and UA (hypotonia). Numerous studies have found that 50-60% of children with DS have OSA. When children with DS mature, they maintain their anatomic abnormalities and generalized hypotonia with recent studies showing the overall incidence of OSA among DS patients increases as they become adults: 94% of adults with DS were found to have OSA, 88% had at least moderate OSA (AHI>15), and 69% had severe OSA (AHI>30). In addition, while it is well known that CPAP compliance is low in normal adults, it is even more difficult for children and adults with a developmental disability to comply with CPAP. Partially due to the low compliance with CPAP, surgery is often recommended for those with DS who have OSA. However, in some patients with DS, routine tonsillectomy and adenoidectomy does not resolve obstructive respiratory issues. We believe our innovation could be an attractive alternative treatment option for this highly vulnerable and often overlooked sub-population with OSA. It may have applicability in other craniofacial and neurologic conditions as well.

Snoring is a common sound made mainly on inspiration during sleep. 45% of adults snore at least occasionally and 25% snore chronically. Snoring can severely disturb the sleep of both patients and their bed partners. During sleep, the UA dilator muscle relaxes, narrowing the airway and increasing airflow resistance. During inhalation, the inflow of air passes from the wider opening of the mouth to the narrower pharynx. This narrowing makes the air move faster and as it passes over the structures of the pharynx and the resulting reduced air pressure pulls (sucks) the tissue into the lumen of the pharynx. During wakefulness, the dilatory force of the UA musculature keeps the pharyngeal tissue from vibrating. However, during sleep, there is a reduction of UA dilator activation and hence reduced dilation force. This makes the pharyngeal tissue more susceptible to the pulling power of reduced airway pressure. As the soft tissue is pulled into the lumen, the elasticity of the soft tissue reaches its limit and the tissue's elasticity pulls it back into place. This vibration of the pharyngeal tissue—into the lumen and out again—produces the snoring sound. While many of the pharyngeal structures, such as the soft palate, pharyngeal walls, epiglottis and tongue, may vibrate and contribute to snoring, the vibration of the soft palate is the structure most responsible for snoring.

The sleep of snorers as well as those with increased UA resistance generally may be fragmented due to transient arousals triggered by the snoring sound itself or increased airway resistance. Patients with Respiratory Effort Related Arousals (RERAs) or snoring arousals may present with sleep fragmentation that rivals that seen in severe apnea (without the associated oxygen desaturations). They can therefore be similarly susceptible to increased risks for motor vehicle and workplace accidents.

Snoring is more common in males and increases with age. Although women do not snore as frequently as men, there is a parallel increase in snoring prevalence with increasing age in women. Snoring is a common complaint of bed partners. Snoring can be quite loud and in the context of the usually quiet sleeping environment, the sound can be quite disturbing.

Increasing the caliber of the UA lumen reduces or eliminates snoring. Weight reduction, for example, is known to increase the cross sectional area of the UA. It is well known that weight loss can improve snoring. Similarly, UA surgery reduces the tissue crowding the UA lumen and reliably reduces or eliminates snoring. In contrast, reducing the caliber of the UA lumen increases snoring. Weight gain, weakness of the UA dilator muscles (as produced by alcohol, benzodiazepines, and sleep deprivation) and sleeping in the supine position can make snoring louder and more frequent.

Other measures employed to address snoring include ear plugs for the bed partner, white noise generators to mask the snoring sound, moving the snorer from the supine to a lateral sleeping position, and waking the snorer to temporarily restore UA dilator strength. However, these measures are usually not completely satisfactory. We believe toning of the UA musculature via targeted tongue strengthening may reduce snoring. Several recent studies have shown that oropharyngeal exercises are effective at reducing objectively measured snoring. In one study, 53 snorers performed oropharyngeal exercises for 30 minutes a day, 5 days a week, over a 3 month period. The mean Snoring Scale Score (SSS) was significantly reduced (7.01 to 3.09, $P=0.0001$). In a RCT, the group assigned to perform daily oropharyngeal exercises saw a significant decrease in the Snore Index (the number of snores per hour that exceed an intensity of 36 dB), from 60.4 to 31.0, $P=0.033$ and the Total Snore Index (the total number of snores per hour), from 99.5 to 48.2, $P=0.017$.

An effective way to strengthen the GG and the UA may also prove useful in the treatment of speech disorders. It may prolong speech function in patients with degenerative disorders such as ALS (Lou Gehrig's disease) and serve as a rehabilitative tool, e.g., for stroke victims and head and neck cancer patients, to recover speaking abilities. Just as oropharyngeal exercises borrowed from the field of speech pathology have proven effective in the treatment of OSA, we believe the reverse is true as well: that our simple to use training method may substantially improve speech functioning. This hypothesis is supported by the fact that non-speech oral motor exercises are a standard in speech therapy, with tongue protrusion one of the most common exercises employed by speech pathologists.

Dysphagia (difficulty swallowing) is a potentially life-threatening condition that can emerge as a consequence of numerous medical conditions that disturb the neural and motor systems underlying swallowing function. There is a much greater prevalence of dysphagia among the neurologically impaired, those with head and neck cancer, and the elderly. Irrespective of etiology, the potential health risks of dysphagia are significant and include increased likelihood for malnutrition, pulmonary infection, and death. Dysphagia can also negatively impact medical recovery, resulting in longer hospitalizations and an increased need for long-term care. Dysphagia can lead to aspiration of food particles or liquids, which in turn can lead to pneumonia. This is a disconcertingly common problem among residents of assisted care facilities and nursing homes and is a frequent cause for hospitalization. To prevent infection, elderly patients are often restricted to a very bland and easy-to-swallow diet (which results in disinclination toward eating and undesirable weight loss, increasing frailty, and greater risk of falls with associated fractures) or have a feeding tube implanted. Oropharyngeal exercises have successfully been used as a treatment for dysphagia.

As used herein, the term "about" or "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation. Similarly, the word "or" is intended to include "and" unless the context clearly indicates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed:

1. A device for strengthening a genioglossus muscle of a user to treat sleep apnea, the device comprising:
   a mouthpiece comprising:
      a force transducer; and
      a pusher plate coupled with the force transducer, wherein the pusher plate is configured to transfer a force applied to the pusher plate to the force transducer; and
   a control module comprising at least one processor configured to:
   receive a first signal from the force transducer, the first signal indicating a first force applied to the pusher plate by the genioglossus muscle of the user;
   set a baseline maximum tongue protrusive force (TPFmax) of the user based on the first signal;
   set a target force of the mouthpiece that is less than the TPFmax;
   receive a plurality of second signals from the force transducer, each of the plurality of second signals indicating a training force applied to the pusher plate;
   determine that an exercise has commenced based on the training force exceeding the target force;
   determine an elapsed time of the exercise;
   generate an indicator of completion of the exercise responsive to the elapsed time of the exercise satisfying a predetermined threshold time; and
   generate a prompt that requests the user to repeat the exercise a predetermined number of times.

2. The device of claim 1; the mouthpiece further comprises a plurality of grooves configured to receive a user's tooth.

3. The device of claim 2, wherein each of the plurality of grooves has a unique number corresponding to depths inside an oral cavity of the user.

4. The device of claim 3, wherein the control module is further configured to receive, via an input device, the unique number corresponding to each of the plurality of grooves.

5. The device of claim 4, wherein the input device is a pushbutton of the mouthpiece.

6. The device of claim 2, wherein each of the plurality of grooves is angled between about 0 degrees and about 20 degrees from a vertical axis.

7. The device of claim 1, wherein the force transducer is a piezoresistive compression load cell.

8. The device of claim 1, wherein the force transducer has a dynamic range of between about 0 and about 25 lbf.

9. The device of claim 1, wherein a housing of the mouthpiece comprises polylactide plastic.

10. The device of claim 1, wherein the pusher plate is removable from the mouthpiece.

11. The device of claim 1, wherein the pusher plate comprises a textured surface.

12. The device of claim 1, wherein the mouthpiece is disposable.

13. The device of claim 1, wherein the device further comprises a display, wherein the at least one processor is further configured to transmit to the display, while receiving the plurality of second signals, the training force and the elapsed time of exercise, wherein the indicator is a first indicator, wherein the first indicator is a first color, and wherein the at least one processor is further configured to generate a second indicator of a second color while receiving the plurality of second signals, the second color being different from the first color.

14. A method of administering a treatment for sleep apnea, the method comprising:
    identifying a subject with obstructive sleep apnea (OSA);
    strengthening a genioglossus muscle of the subject by:
        providing the subject with a mouthpiece that is coupled to a control module, the mouthpiece including a force transducer coupled with a pusher plate;
        identifying, by the control module, from a plurality of first signals received from the force transducer, a baseline maximum tongue protrusive force (TPFmax) applied to the pusher plate by the genioglossus muscle of the subject;
        setting, by the control module, a target force of the mouthpiece, the target force being indexed to less than the TPFmax;
        identifying, by the control module, from a plurality of second signals received from the force transducer, a training force applied to the pusher plate by the genioglossus muscle of the subject;
        determining, by the control module, that an exercise has commenced based on the training force exceeding the target force;
        determining, by the control module, an elapsed time of the exercise;
        providing, by the control module, an indicator of when to end the exercise responsive to the elapsed time of the exercise satisfying a predetermined threshold time; and
        generating, by the control module, a prompt that requests the subject to repeat the exercise a predetermined number of times.

15. The method of claim 14, wherein the mouthpiece further comprises a plurality of grooves configured to receive a patient's tooth.

16. The method of claim 15, wherein each of the plurality of grooves has a number corresponding to a depth inside an oral cavity of the subject.

17. The method of claim 16, further comprising receiving, via an input device, the number corresponding to each of the plurality of grooves.

18. The method of claim 16, further comprising repeating the exercise in more than one of the plurality of grooves.

19. The method of claim 16, wherein the TPFmax is a first TPFmax, wherein the target force is a first target force, wherein the training force is a first training force, wherein the exercise is a first exercise, wherein the elapsed time is the elapsed time of the first exercise, wherein the predetermined threshold time is a first predetermined threshold time, the method further comprising:
    receiving, via an input device, a first number corresponding to a first groove of the plurality of grooves;
    providing, by the control module, based on the received first number, a first subset of data comprising the first exercise;
    receiving, via the input device, a second number, corresponding to a second groove of the plurality of grooves;
    identifying, by the control module, from a plurality of third signals received from the force transducer, a second TPFmax applied to the pusher plate by the genioglossus muscle of the subject;
    setting, by the control module, a second target force of the mouthpiece, the second target force being indexed to less than the second TPFmax;
    identifying, by the control module, from a plurality of fourth signals received from the force transducer, a second training force applied to the pusher plate by the genioglossus muscle of the subject;
    determining, by the control module, a second exercise has commenced based on the second training force exceeding the second target force;
    determining, by the control module, an elapse time of the second exercise;
    providing, by the control module, a second indicator of when to end the second exercise responsive to the elapsed time of the second exercise satisfying a second predetermined threshold time; and
    providing, by the control module, a second indicator of when to end the second exercise responsive to the elapsed time of the second exercise satisfying a second predetermined threshold time; and
    providing, by the control module, a second subset of data comprising the second exercise.

20. The method of claim 14, wherein identifying the subject with OSA comprises determining a respiratory disturbance index (RDI) while the subject sleeps.

21. The method of claim 20, further comprising measuring a change in the RDI following the exercise.

22. The method of claim 14, wherein the force transducer has a dynamic range of between about 0 and 25 lbf.

23. The method of claim 14, further comprising providing, by the control module, a computer-based game in which the subject earns a score based on the training force so as to motivate the subject to train.

24. A method to treat obstructive sleep apnea of a user by strengthening a genioglossus muscle of the user, the method comprising:
    providing the user with a mouthpiece that is coupled to a control module and that comprises a force transducer coupled to a pusher plate, the mouthpiece further comprising a plurality of grooves configured to receive one or more teeth of the user, wherein each of the plurality of grooves corresponds to a depth inside an oral cavity of the user;
    determining a baseline maximum tongue protrusive force (TPFmax) for the user based on a first signal from the force transducer, the first signal indicating a first force applied to the pusher plate by the genioglossus muscle of the user;
    setting, via the control module, a target force that is less than the TPFmax;
    detecting, via the force transducer, a training force applied to the pusher plate by the user;

determining, by the control module, that an exercise has commenced based on the training force exceeding the target force;

determining, by the control module, an elapsed time of the exercise;

generating, by the control module, an indicator indicating a completion of the exercise responsive to the elapsed time of the exercise satisfying a predetermined threshold time.

25. The method of claim 24, wherein each of the plurality of grooves has a number corresponding to the depth inside the oral cavity of the user.

26. The method of claim 25, further comprising receiving, via an input device, the number corresponding to each of the plurality of grooves.

27. The method of claim 26, wherein the input device is a pushbutton.

28. The method of claim 25, wherein the TPFmax is a first TPFmax, wherein the target force is a first target force, wherein the training force is a first training force, and wherein the exercise is a first exercise, and method further comprising:

receiving, via an input device, a first number corresponding to a first groove of the plurality of grooves;

providing, by the control module, based on the received first number, a first subset of data comprising the first TPFmax, the first target force, and the first training force;

receiving, via the input device, a second number corresponding to a second groove of the plurality of grooves;

identifying, by the control module, from a plurality of third signals received from the force transducer, a second TPFmax applied to the pusher plate by the genioglossus muscle of the subject;

setting, by the control module, a second target force of the mouthpiece, the second target force being indexed to less than the second TPFmax;

identifying, by the control module, from a plurality of fourth signals received from the force transducer, a second training force applied to the pusher plate by the genioglossus muscle of the subject; and providing, by the control module, a second subset of data comprising the second TPFmax, the second target force, and the second training force.

29. The method of claim 24, further comprising identifying the user as having obstructive sleep apnea (OSA) by determining an RDI for the user while the user sleeps.

* * * * *